(12) United States Patent
Xi (10) Patent No.: US 10,080,524 B1
(45) Date of Patent: Sep. 25, 2018

(54) WEARABLE THERMOMETER PATCH COMPRISING A TEMPERATURE SENSOR ARRAY

(71) Applicant: VivaLnk, Inc., Santa Clara, CA (US)

(72) Inventor: Cecilia Xi, San Jose, CA (US)

(73) Assignee: VivaLnk, Inc., Santa Clara, CA (US)

( * ) Notice: Subject to any disclaimer, the term of this patent is extended or adjusted under 35 U.S.C. 154(b) by 0 days.

(21) Appl. No.: 15/848,464

(22) Filed: Dec. 20, 2017

Related U.S. Application Data (63) Continuation-in-part of application No. 15/835,781, filed on Dec. 8, 2017.

(51) Int. Cl.
| | | |
|---|---|---|
| G01K 13/02 | (2006.01) | |
| A61B 5/00 | (2006.01) | |
| A61B 5/01 | (2006.01) | |

(52) U.S. Cl.
CPC .......... *A61B 5/4842* (2013.01); *A61B 5/0008* (2013.01); *A61B 5/01* (2013.01); *A61B 5/4836* (2013.01); *A61B 5/6833* (2013.01); *A61B 2560/0412* (2013.01); *A61B 2560/0475* (2013.01); *A61B 2562/0271* (2013.01); *A61B 2562/043* (2013.01); *A61B 2562/164* (2013.01); *A61B 2562/227* (2013.01)

(58) Field of Classification Search
CPC . A61B 5/01; A61B 5/445; A61B 2017/00084; A61B 2046/205; A61B 5/0008; A61B 5/015; A61B 5/0531; G01K 13/002; G01K 13/02; A61M 2205/3368; A61M 2230/50; A61M 5/3157

USPC ........ 374/120, 163, 100, 170, 137, 110, 112
See application file for complete search history.

(56) References Cited

U.S. PATENT DOCUMENTS

| | | | | |
|---|---|---|---|---|
| 3,339,542 | A | * | 9/1967 | Howell .................... A61B 5/01 29/610.1 |
| 5,749,365 | A | | 5/1998 | Magill |
| 5,820,263 | A | * | 10/1998 | Ciobanu .................. A61B 5/01 374/111 |
| 6,220,750 | B1 | * | 4/2001 | Palti .......................... G01K 1/16 374/164 |
| 8,303,172 | B2 | * | 11/2012 | Zei ....................... A61B 5/0507 374/120 |
| 8,609,168 | B2 | * | 12/2013 | Ceravalls Pujol ....... G01K 1/14 374/10 |
| 9,132,031 | B2 | * | 9/2015 | Levinson ................... A61F 7/10 |
| 9,974,472 | B2 | * | 5/2018 | Hayter ..................... A61B 5/01 |
| 2007/0010861 | A1 | * | 1/2007 | Anderson .............. A61B 5/415 607/96 |
| 2007/0270672 | A1 | | 11/2007 | Hayter |
| 2009/0171180 | A1 | | 7/2009 | Pering |

(Continued)

FOREIGN PATENT DOCUMENTS

WO          WO8404237 A * 4/1984

*Primary Examiner* — Gail Kaplan Verbitsky
(74) *Attorney, Agent, or Firm* — SV Patent Service (57) ABSTRACT

A wearable thermometer patch for monitoring healing of a wound on a user's skin includes a circuit substrate comprising an electric circuit and a plurality of temperature probe units distributed in a two-dimensional array. Each of the plurality of temperature probe units can include a temperature sensor in electric connection with the electric circuit in the circuit substrate. The plurality of temperature probe units can measure temperature values on a user's skin at different positions defined by the two-dimensional array.

20 Claims, 7 Drawing Sheets

(56) References Cited

U.S. PATENT DOCUMENTS

| | | | |
|---|---|---|---|
| 2009/0204100 A1* | 8/2009 | Van Pieterson | A61B 5/0008 604/503 |
| 2010/0030099 A1* | 2/2010 | Fraden | A61B 5/00 600/549 |
| 2010/0239648 A1 | 9/2010 | Smith | |
| 2010/0331834 A1* | 12/2010 | Peterson | A61B 18/1477 606/41 |
| 2012/0242481 A1 | 9/2012 | Gernandt | |
| 2013/0158376 A1* | 6/2013 | Hayter | A61B 5/01 600/347 |
| 2013/0310661 A1 | 11/2013 | Jebwab | |
| 2014/0012102 A1 | 1/2014 | Das | |
| 2017/0319378 A1* | 11/2017 | Anderson | A61B 5/415 |
| 2018/0133499 A1* | 5/2018 | Dronov | A61N 1/403 |
| 2018/0153760 A1* | 6/2018 | Rosen | A61F 7/10 |

\* cited by examiner

WEARABLE THERMOMETER PATCH COMPRISING A TEMPERATURE SENSOR ARRAY

BACKGROUND OF THE INVENTION

The present application relates to wearable electronic devices, and in particular, to wearable thermometer patches that can measure human skin temperatures near wounds.

Ambulatory temperature monitoring of local skin are of great importance for wound healing. Local skin temperature can change noticeably due to local inflammation and perfusion. During the healing process of the wound, local temperature becomes higher than surroundings, and then gradually drops. If temperature elevation is observed for a longer duration than expected, it indicates extended inflammation and possible infection, which impacts normal healing process, so appropriate anti-infective agents or additional management may be needed.

Past researches have shown that skin temperatures can be measured by image sensors that are sensitive in the IR spectral range. This type of equipment is normally bulky and cannot be easily carried by users. Their measurements are also intermittent and require users to stop their other daily activities. In addition, it requires advanced equipment or algorithmic processing of the data.

Products for monitoring wound healing are not known in the market. A smart suture developed by Professor John Roger has been tested to monitor wound infection on a rat model. However, suture is not necessary or suitable for all wounds.

There is therefore a long-felt need for a convenient, portable, low-cost, and noninvasive device that can monitor wound healing on human skin without affecting user's daily activities, and suitable for different types of wounds.

SUMMARY OF THE INVENTION

The presently disclosure attempts to provide a convenient and portable solution that can continuously monitor the process of wound healing on human skin. The presently disclosed wearable wireless thermometer patch that can be attached to human skin near a wound to conduct temperature measurements, which can continuously monitor the healing progress and notify the doctor promptly for abnormal healing process. The disclosed wearable wireless thermometer patch is convenient to wear, noninvasive, low-cost, and suitable for different types of wounds. The disclosed wearable wireless thermometer patch allows the user to conduct his or her usual daily activities.

In the presently disclosed wearable wireless thermometer patch is flexible, breathable, and stretchable, which are thus comfortable to wear. The disclosed wearable thermometer patches are capable wireless communication with little interference from users' skins.

In one general aspect, the present invention relates to a wearable thermometer patch for monitoring temperature on a user's skin, including: a circuit substrate comprising an electric circuit; a first temperature probe unit that includes a first temperature sensor in electric connection with the electric circuit in the circuit substrate, wherein the first temperature probe unit can include a first protruded portion below the circuit substrate; and a second temperature probe unit can include a second temperature sensor in electric connection with the electric circuit in the circuit substrate, wherein the second temperature probe unit cam include a second protruded portion below the circuit substrate, wherein the first protruded portion and the second protruded portion can have different protrusion lengths below the circuit substrate, wherein the first temperature probe unit and the second temperature probe unit can measure temperature values at different depths into the user's skin.

Implementations of the system may include one or more of the following. The wearable thermometer patch can further include a third temperature probe unit that can include a third temperature sensor in electric connection with the electric circuit, wherein the third temperature probe unit can include a third protruded portion below the circuit substrate. The wearable thermometer patch can further include a lower layer below the circuit substrate, wherein the circuit substrate and the lower layer include through holes in which the first temperature probe unit and the second temperature probe unit can be respectively mounted, wherein the first protruded portion and the second protruded portion can be respectively in contact with the user's skin at different positions. The wearable thermometer patch can further include an elastic layer on the circuit substrate, the first temperature probe unit, and the second temperature probe unit; and an adhesive material under the lower layer and configured to bond the lower layer to the user's skin. The first temperature probe unit can include a thermally conductive cup having a bottom portion that can be in contact with the user's skin, wherein the first temperature sensor is placed inside and in thermal conduction with the thermally conductive cup. The wearable thermometer patch can further include a semiconductor chip mounted on the circuit substrate and in electric connection with the electric circuit, wherein the semiconductor chip can receive a first electrical signal from the first temperature sensor in response to a first measured skin temperature at the first position, wherein the semiconductor chip can receive a second electrical signal from the second temperature sensor in response to a second measured skin temperature at the second position. The wearable thermometer patch can further include an antenna mounted on the circuit substrate and in electric connection with the semiconductor chip, wherein the antenna can wirelessly send temperature measurement data to a control device. The first temperature probe unit can be located at a first position along a first direction, wherein the second temperature probe unit is located at a second position along the first direction, wherein the wearable thermometer patch is to be attached near a wound on a user's skin with the first direction is toward or away from the wound, wherein a temperature gradient can be calculated based on the temperature values at the different distances. The first direction can be substantially perpendicular to the wound on the user's skin.

In another general aspect, the present invention relates to a wearable thermometer patch for monitoring temperature on a user's skin includes a circuit substrate comprising an electric circuit; and a plurality of temperature probe units distributed in a two-dimensional array, wherein each of the plurality of temperature probe units can include a temperature sensor in electric connection with the electric circuit in the circuit substrate, wherein the plurality of temperature probe units can measure temperature values on a user's skin at different positions defined by the two-dimensional array.

Implementations of the system may include one or more of the following. The plurality of temperature probe units can include at least four temperature probe units. The wearable thermometer patch can further include lower layer below the circuit substrate, wherein the circuit substrate and the lower layer include through holes in which the plurality of temperature probe units can be respectively mounted, wherein the plurality of temperature probe units can include portions respectively that are in contact with the user's skin. The wearable thermometer patch can further include an elastic layer on the circuit substrate, and the plurality of temperature probe units; and an adhesive material under the lower layer and configured to bond the lower layer to the user's skin. One of the plurality of temperature probe units can include a thermally conductive cup having a bottom portion that can be in contact with the user's skin, wherein the one of one of the plurality of temperature probe units can be placed inside and in thermal conduction with the thermally conductive cup. The wearable thermometer patch can further include a semiconductor chip mounted on the circuit substrate and in electric connection with the electric circuit, wherein the semiconductor chip can receive electrical signals from the plurality of temperature probe units in response to skin temperatures measured at different positions on the user's skin. The wearable thermometer patch can further include an antenna mounted on the circuit substrate and in electric connection with the semiconductor chip, wherein the antenna can wirelessly send temperature measurement data to a control device. The wearable thermometer patch can be attached near a wound on a user's skin, wherein a temperature gradient can be calculated based on the temperature values measured by the plurality of temperature probe units. The temperature gradient can be calculated by a semiconductor chip in the circuit substrate or by a control device in communication with the electric circuit. The wearable thermometer patch can further include a treatment portion that can apply heat, an electrical signal, or a force or a pressure to user's skin to assist healing of the wound.

In another general aspect, the present invention relates to a wearable thermometer patch for monitoring healing of a wound on a user's skin, including: a circuit substrate that includes an electric circuit; a first temperature probe unit that includes a first temperature sensor in electric connection with the electric circuit in the circuit substrate, wherein the first temperature probe unit is located at a first position along a first direction; and a second temperature probe unit comprising a second temperature sensor in electric connection with the electric circuit in the circuit substrate, wherein the second temperature probe unit is located at a second position along the first direction, wherein the wearable thermometer patch is to be attached near a wound on a user's skin with the first direction is toward or away from the wound, wherein the first temperature probe unit and the second temperature probe unit can measure temperature values at different distances from the wound on the user's skin, wherein a temperature gradient is calculated based on the temperature values at the different distances.

Implementations of the system may include one or more of the following. The first direction can be substantially perpendicular to the wound on the user's skin. The wearable thermometer patch can further include a third temperature probe unit comprising a third temperature sensor in electric connection with the electric circuit, wherein the third temperature probe unit is located at a third position along the first direction, wherein the temperature gradient is calculated further based on temperature values measured by the third temperature probe unit. The first temperature probe unit, the second temperature probe unit, and the third temperature probe unit can be positioned along a substantially straight line in the first direction. The wearable thermometer patch can further include a lower layer below the circuit substrate, wherein the circuit substrate and the lower layer include through holes in which the first temperature probe unit and the second temperature probe unit are respectively mounted, wherein the first temperature probe unit and the second temperature probe unit include portions respectively can be in contact with the user's skin. The wearable thermometer patch can further include an adhesive material under the lower layer and configured to bond the lower layer to the user's skin. The first temperature probe unit can include a thermally conductive cup having a bottom portion that can be in contact with the user's skin, wherein the first temperature sensor is placed inside and in thermal conduction with the thermally conductive cup. The wearable thermometer patch can further include a semiconductor chip mounted on the circuit substrate and in electric connection with the electric circuit, wherein the semiconductor chip can receive a first electrical signal from the first temperature sensor in response to a first measured skin temperature at the first position, wherein the semiconductor chip can receive a second electrical signal from the second temperature sensor in response to a second measured skin temperature at the second position. The wearable thermometer patch can further include an antenna mounted on the circuit substrate and in electric connection with the semiconductor chip, wherein the antenna can wirelessly send temperature measurement data or the temperature gradient to a control device. The temperature gradient can be calculated on the control device based on the first measured skin temperature and the second measured skin temperature. The semiconductor chip can calculate the temperature gradient based on the first measured skin temperature and the second measured skin temperature. The wearable thermometer patch can further include a treatment portion that can apply heat, an electrical signal, or a force or a pressure to user's skin to assist healing of the wound. The wearable thermometer patch can further include an elastic layer on the circuit substrate, the first temperature probe unit, and the second temperature probe unit.

In another general aspect, the present invention relates to a portable system for monitoring healing of a wound on a user's skin, including: a wearable thermometer patch attached near a wound on a user's skin, comprising: a circuit substrate comprising an electric circuit; a first temperature probe unit comprising a first temperature sensor in electric connection with the electric circuit in the circuit substrate, wherein the first temperature probe unit is located at a first position along a first direction; and a second temperature probe unit comprising a second temperature sensor in electric connection with the electric circuit in the circuit substrate, wherein the second temperature probe unit is located at a second position along the first direction, wherein the wearable thermometer patch is so positioned that the first direction is toward or away from the wound, wherein the first temperature probe unit and the second temperature probe unit that can measure temperature values at different distances from the wound on the user's skin; and a control device that can control temperature measurements by the first temperature probe unit and the second temperature probe unit, wherein a temperature gradient is calculated based on the temperature values at the different distances.

Implementations of the system may include one or more of the following. The wearable thermometer patch can further include an antenna mounted on the circuit substrate and in electric connection with the semiconductor chip, wherein the antenna can wirelessly send temperature measurement data or the temperature gradient to the control device. The control device can calculate the temperature gradient based on the first measured skin temperature and the second measured skin temperature. The wearable thermometer patch further can include a semiconductor chip mounted on the circuit substrate and in electric connection with the electric circuit, wherein the semiconductor chip can receive a first electrical signal from the first temperature sensor in response to a first measured skin temperature at the first position, wherein the semiconductor chip can receive a second electrical signal from the second temperature sensor in response to a second measured skin temperature at the second position, wherein the semiconductor chip can calculate the temperature gradient based on the first measured skin temperature and the second measured skin temperature. The first direction can be substantially perpendicular to the wound on the user's skin. The wearable thermometer patch can further include a third temperature probe unit comprising a third temperature sensor in electric connection with the electric circuit, wherein the third temperature probe unit is located at a third position along the first direction, wherein the temperature gradient is calculated further based on temperature values measured by the third temperature probe unit.

In another general aspect, the present invention relates to a portable system for monitoring healing of a wound on a user's skin, including: a plurality of wearable thermometer patches attached near a wound on a user's skin, wherein at least one of plurality of wearable thermometer patches includes: a circuit substrate comprising an electric circuit; multiple temperature probe units each comprising a temperature sensor in electric connection with the electric circuit in the circuit substrate, wherein the multiple temperature probe unit are located at different positions along a first direction, wherein the wearable thermometer patch is so positioned that the first direction is toward or away from the wound, wherein the multiple temperature probe units can measure temperature values at different distances from the wound on the user's skin; and a control device that can control temperature measurements by the multiple temperature probe units, wherein a temperature gradient can be calculated based on the temperature values at the different distances from the wound at the at least one of the plurality of wearable thermometer patches.

These and other aspects, their implementations and other features are described in detail in the drawings, the description and the claims.

DETAILED DESCRIPTION OF THE INVENTION

Figure 1:
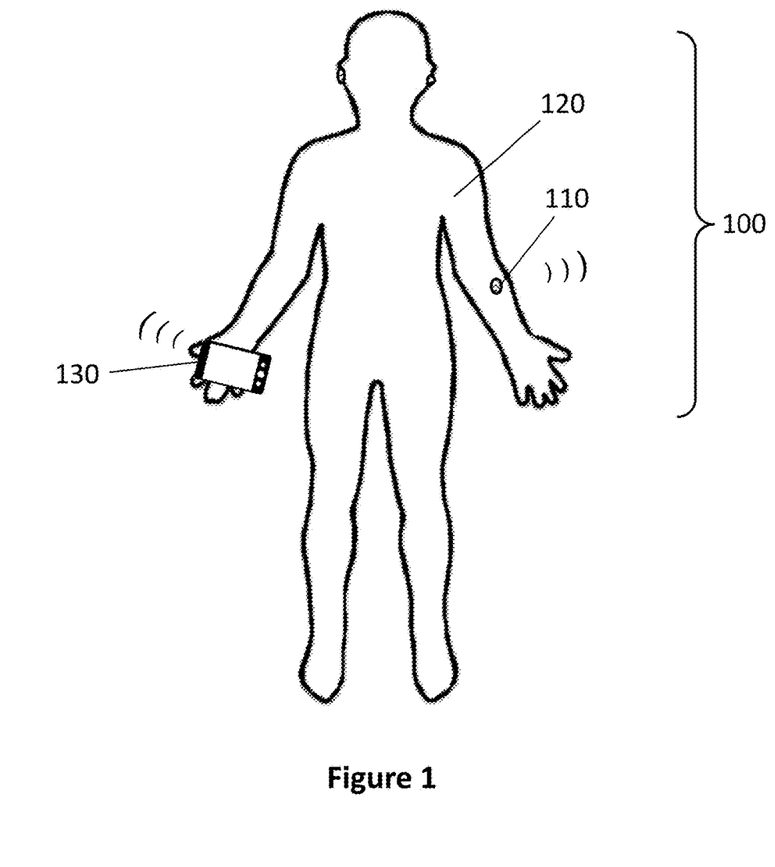
FIG. 1 illustrates the usage of a wearable thermometer patch attached to a user's skin.
Figure 2:
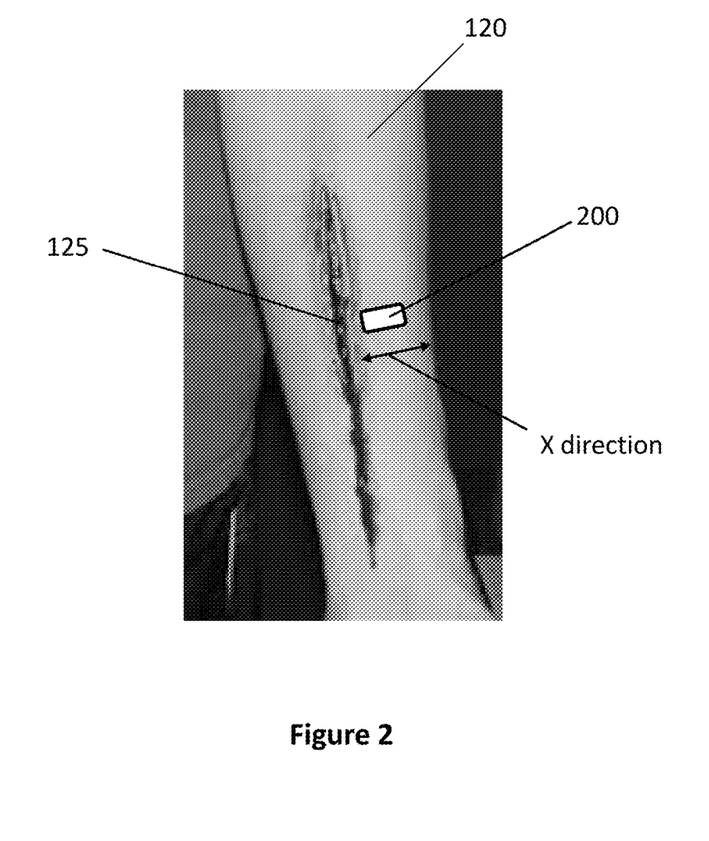
FIG. 2 illustrates a wearable thermometer patch properly positioned next to a wound on a user's skin in accordance with some embodiments of the present invention.

Referring to FIGS. 1 and 2, a system 100 includes at least one wearable thermometer patch 200 and a wireless control device 130. The wearable thermometer patch 200 is attached to the skin 120 of a user for measuring skin temperature and optionally other body vital signs. The wearable thermometer patch 200 can be placed near a wound 125 on the skin 120 to monitor the healing process and progress of the wound 125. In the present disclosure, the term "wearable thermometer patch" can also be referred to as "wearable sticker", "wearable tag", or "wearable band", etc. The wearable thermometer patch 200 can be attached to the skin with adhesives or held to be in contact with the skin by a band wrapped around a user's arm, ankle, or a leg. In some embodiments, the wearable thermometer patches disclosed in the present application can be implemented as part of a wound dressing. Wound dressing is usually disposed and replaced regularly (e.g. daily, twice a day, etc.). The disclosed wearable thermometer patches and control devices can continuously monitor skin temperature at one or multiple locations, in a two dimensional area, and/or at different depths into user's skin.

Figure 3:
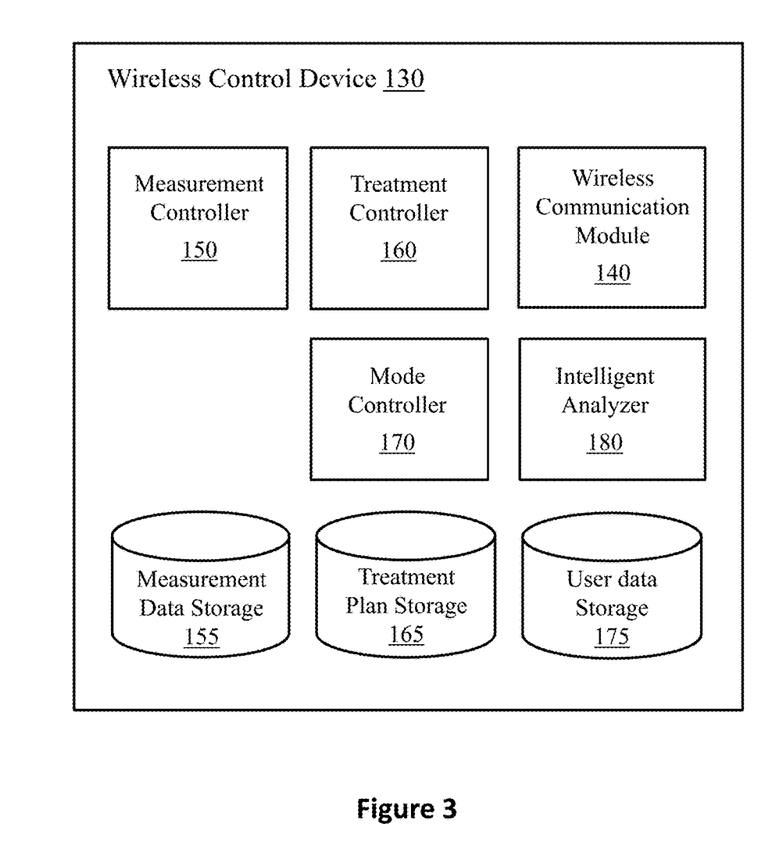
FIG. 3 is a system block diagram for a wireless control device in wireless communications of the wearable thermometer patch in accordance with some embodiments of the present invention.

Referring to FIGS. 1 and 3, the wireless control device 130 can wirelessly exchange data with the wearable thermometer patch 200. The wireless communications can be conducted using Wi-Fi, Bluetooth, Zigbee, and other wireless communication technologies and protocols. The wireless control device 130 can be a portable mobile device, which a user can carry with him or her. The wireless control device 130 can also be a stationary device that can be placed at home or office where the user may stay for an extended period. The portable mobile device can be implemented with specialized hardware and software units built in a smart phone, a tablet computer (including devices such as iPod), or a dedicated health or sport monitoring device. The wireless control device 130 can be in communication with a network server in which a user account is stored for the user.

In some embodiments, the wearable thermometer patch 200 can conduct one or more types of measurements on the user' skin or body. In addition to measuring skin temperature, the wearable thermometer patch 200 can include sensors that sense a variety of signals such as electric voltage, galvanic skin response, blood pressure, heart rate, force, acceleration, blood oxygen level, blood glucose level, etc. The wearable thermometer patch 200 can also include a treatment portion for applying treatments to the user's skin or body. The treatment portion can apply electrical signals, heat, and sometimes force or pressure to user's body to assist the wound healing process. Details of wearable patches for conducting measurements and treatments are disclosed in commonly assigned co-pending U.S. patent application Ser. No. 15/472,641 titled "Multi-purpose wearable patch for measurement and treatment", filed Mar. 29, 2017, the disclosure of which is incorporated herein by reference.

The wireless control device 130 includes a wireless communication module 140 that can wirelessly communicate with the wearable thermometer patches (200 in FIG. 1) using above described wireless technologies. The wireless control device 130 includes a measurement controller 150 that controls the wireless communication module 140 to transmit measurement control signals to wearable thermometer patches (200 in FIGS. 1 and 4). The measurement controller 150 can vary parameters of the measurements by the wearable thermometer patches. Such measurement parameters can include types, timing, frequencies, durations of measurements, coordination between measurements of the same of different wearable thermometer patches, and coordination between measurements and treatments by the wearable thermometer patches. A measurement data storage 155 stores the measurement data obtained by the wearable thermometer patch 200.

The wireless control device 130 can also includes a treatment controller 160 that can control the treatment functions of the wearable thermometer patches based on a treatment plan stored in the treatment plan storage 165. The treatment controller 160 can control the wireless communication module 140 to transmit treatment control signals to wearable thermometer patch 200. A treatment plan can define types, timing, frequencies, amplitude or power, durations of treatments, coordination between treatments of the same or different wearable thermometer patches, and coordination between treatments and measurements by the wearable thermometer patches.

Still referring to FIGS. 1 and 3, the wireless control device 130 can include a mode controller 170 that can set the wearable thermometer patches in measurement modes and/or treatment modes, or a combination thereof by controlling the treatment unit and the sensing unit. Some treatment and measurements can be conducted in parallel, but some should be implemented in separate time periods. In some applications, a portion of the wearable thermometer patches 200 applies treatments while another portion of the wearable thermometer patches 200 conducts measurements. The coordination between measurement and treatment modes is controlled by the mode controller 170. A user data storage 175 stores user data such as user's weight, height, bone density, historic range for blood pressure, heart beat, body temperature, daily patterns of exercises and rests by the user, sickness or symptoms suffered by the user, etc. In some embodiments, as described below, personalized medical treatment can be applied, sometimes dynamically, based on such user data and physician's prescription. An intelligent analyzer 180 can process and analyze the measurement data from different wearable thermometer patches in reference to the measurement data (in 155), the treatment plan (in 165), and user data (in 175).

Figure 4:
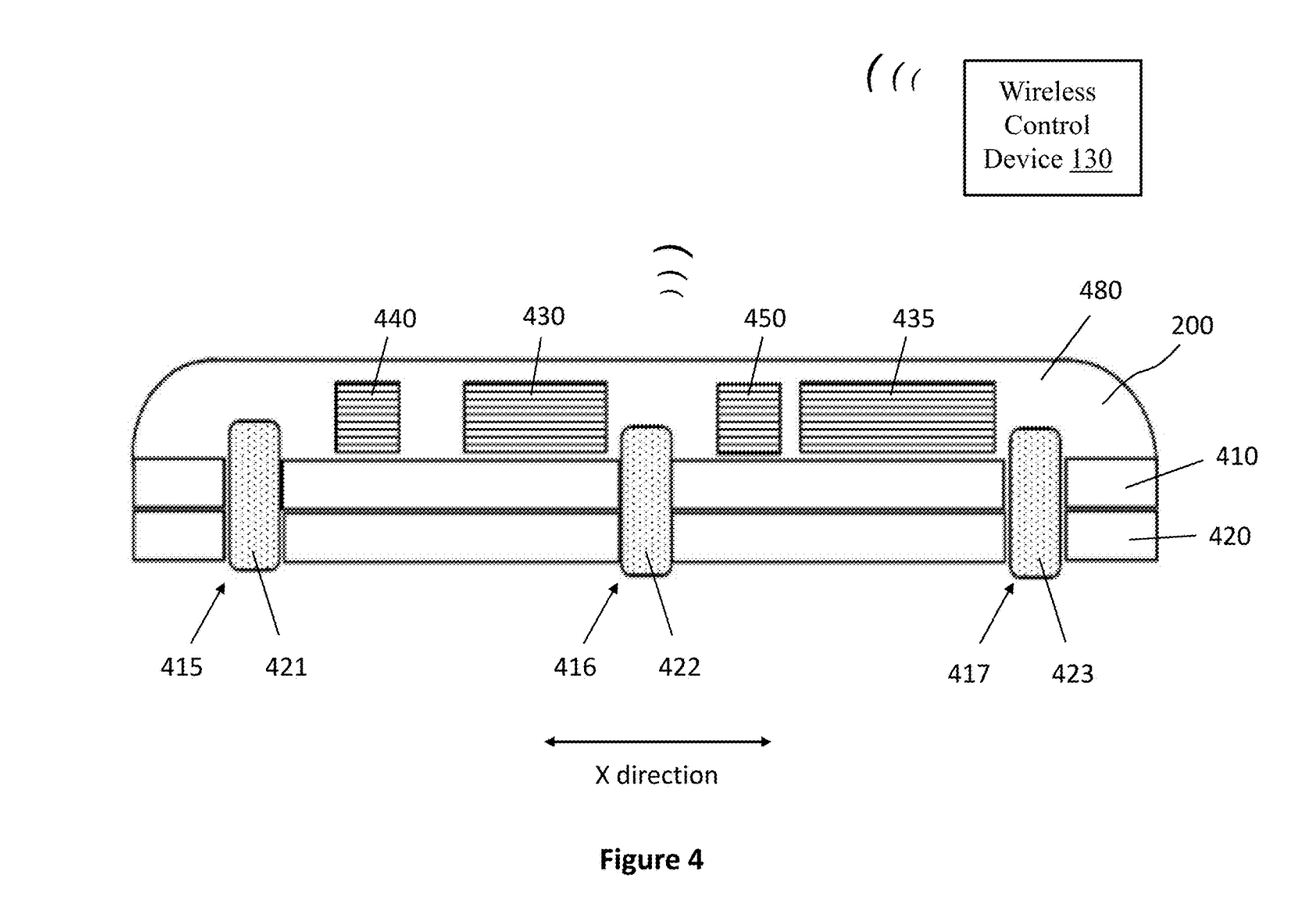
FIG. 4 is a cross-sectional view of a wearable thermometer patch for monitoring wound healing in accordance with some embodiments of the present invention.

Referring to FIG. 4, the wearable thermometer patch 200 includes a flexible circuit substrate 410 and a lower layer 420 under the flexible circuit substrate 410. The lower layer 420 is formed by a soft material such as a perforated polymer material, which can increase comfort when it is in contact with user's skin. Suitable materials for the perforated polymer material include soft materials such as Polyurethane. The flexible circuit substrate 410 and the lower layer 420 include multiple through holes 415-417 and temperature sensor units 421-423 respectively positioned in the through holes 415-417. The temperature sensor units 421-423 are positioned along the x direction. The lower layer 420 is bonded to the bottom surface of the flexible circuit substrate 410 using an adhesive material.

A semiconductor chip 220, a battery 435, an antenna 440, a memory 450, and bonding pads 445 are mounted or formed on the upper surface of the flexible circuit substrate 410. An electric circuit (not shown) is embedded in or formed on flexible circuit substrate 410. The temperature sensor units 421-423, the semiconductor chip 430, the battery 435, the antenna 440, the bonding pads 445, and the memory 450 are connected with the electric circuit in the flexible circuit substrate 410. The battery 435 powers the semiconductor chip 430, the electric circuit, and possibly the temperature sensor units 421-423. The flexible circuit substrate 410 can be made of polymeric materials and built in with the electric circuit that connects the semiconductor chip 430, the battery 435, the antenna 440, the bonding pads 445, and the memory 450.

In some embodiments, the temperature sensor units 421, 422, or 423 can include a thermally conductive cup made of a thermally conductive metallic or alloy material such as copper, stainless steel, ceramic or carbide composite materials. A temperature sensor can be attached to and in thermal conduction with an inner surface near the bottom of the thermally conductive cup. The temperature sensor can be implemented, for example, by a Thermistor, a Resistor Temperature Detector, or a Thermocouple. An adhesive material is applied to a lower surface of the lower layer 420 to attach it to the user's skin. The temperature sensor units 421-423 are thus in tight contact with a user's skin for the accurate temperature measurement of the user's skin. Additionally, the disclosed wearable wireless thermometer patch can include double temperature sensors for correct measurements of human skin temperature. Using double temperature sensors, the temperature can be easily calculated from the Fourier's Law at the thermal equilibrium status, which is independent of the ambient temperature changes.

Further details of wearable thermometer patches are disclosed in the commonly assigned co-pending U.S. patent application Ser. No. 15/224,121 titled "Wearable thermometer patch for accurate measurement of human skin temperature", filed Jul. 29, 2016, and the commonly assigned co-pending U.S. patent application Ser. No. 15/590,657 titled "A wearable thermometer patch capable of measuring human skin temperature at high duty cycle", filed May 9, 2017, the disclosures of which are incorporated herein by reference.

When the bottom portions of the temperature sensor units 421, 422, or 423 are in contact with a user's skin, heat is effectively transferred from the user's skin to the temperature sensors. The temperature sensor units 421, 422, or 423 can send temperature sensing electrical signals to the electric circuit and the semiconductor chip 430. The semiconductor chip 430 processes the electrical signal and outputs another electrical signal, which enables the antenna 440 to transmit a wireless signal to send measurement data to the wireless control device 130.

When the wearable thermometer patch 200 is worn by the user, the antenna 440 is separated from the user's skin by the flexible circuit substrate 410 and the lower layer 420, which minimizes the shielding of the user's body on the transmissions of wireless signals by the antenna 440.

An elastic layer 480 is bonded onto the upper surface of the flexible circuit substrate 410 by an adhesive material. Alternatively, the elastic layer 480 can directly be molded onto the flexible circuit substrate 410 without using a bonding material. The elastic layer 480 includes recesses on the underside to define cavities to contain the antenna 440, the battery 435, and the semiconductor chip 430. The elastic layer 480 also includes holes to allow moisture and sweat from the user's skin to diffuse to the ambient environment, which enhances user's comfort and strength of attachment of the wearable thermometer patch 200 to the user's skin 120.

"The elastic layer 480 can be made of a non-conductive material such as an elastomeric material or a viscoelastic polymeric material having low Young's modulus and high failure strain. In some embodiments, the elastic layer 480 has a Young's Modulus<0.3 Gpa. In some cases, the elastic layer 480 can have Young's Modulus<0.1 Gpa to provide enhanced flexibility and tackability. Materials suitable for the elastic layer 480 include elastomers, viscoelastic polymers, such as silicone, silicone rubber, and medical grade polyurethane that is a transparent medical dressing used to cover and protect wounds with breathability and conformation to skin."

Referring to FIGS. 2 and 4, the temperature sensor units 421, 422, and 423 are displaced at different positions along the x direction. The x direction is toward or away from the wound 125. In one implementation, the temperature sensor units 421, 422, and 423 are positioned substantially along a straight line. In some embodiments, the straight line can be substantially perpendicular to the wound 125. In other implementations, for purpose of efficient packing, for example, the temperature sensor units 421, 422, or 423 are disposed in a triangular form but still having different displacement positions along the x direction. In operation, the wearable thermometer patch 200 is placed on the skin 120 in such an orientation that the temperature sensor units 421, 422, and 423 are positioned at different distances from the wound 125. In one implementation, the wearable thermometer patch 200 is oriented with the associated x direction aligned toward or away from the wound 125. The x direction can be aligned substantially perpendicular to the wound 125. Thus, the temperature sensor units 421, 422, and 423 can measure user's skin temperatures at different locations near the wound 125 during the healing process.

Referring to FIGS. 2-4, skin temperatures can be measured periodically or continuously by the temperature sensor units 421, 422, and 423 at skin locations at different distances from the wound 125. The control data for the temperature measurements can be stored in the memory 450. The temperature measurement data are sent to and recorded in the measurement data storage 155 in the wireless control device 130. The local skin temperatures at different locations measured by the temperature sensor units 421, 422, and 423 can be stored in the memory 450 and are used to calculate a temperature gradient as a function of the distance from the wound 125. The calculation can be conducted by firmware on the wearable thermometer patch 200 or software on the wireless control device 130. During the healing process, the temperature at a skin location closer to the wound is higher than that at a skin location further away from the wound, that is, the temperature gradient is positive toward the wound. The temperature gradient will gradually decrease to below a threshold (reflecting natural skin temperature variations) as the wound heals to a complete recovery.

The treatment plan storage 165 can store a normal range for the temperature gradient as a function of healing time for the skin temperatures near a wound. If the intelligent analyzer 190 determines that the calculated temperature gradient based on the measured temperature data is not within a normal range at a specific healing time, the wireless control device 130 can send out an alert to the user or a medical professional. The treatment control data can be stored in the memory 450.

Figure 5:
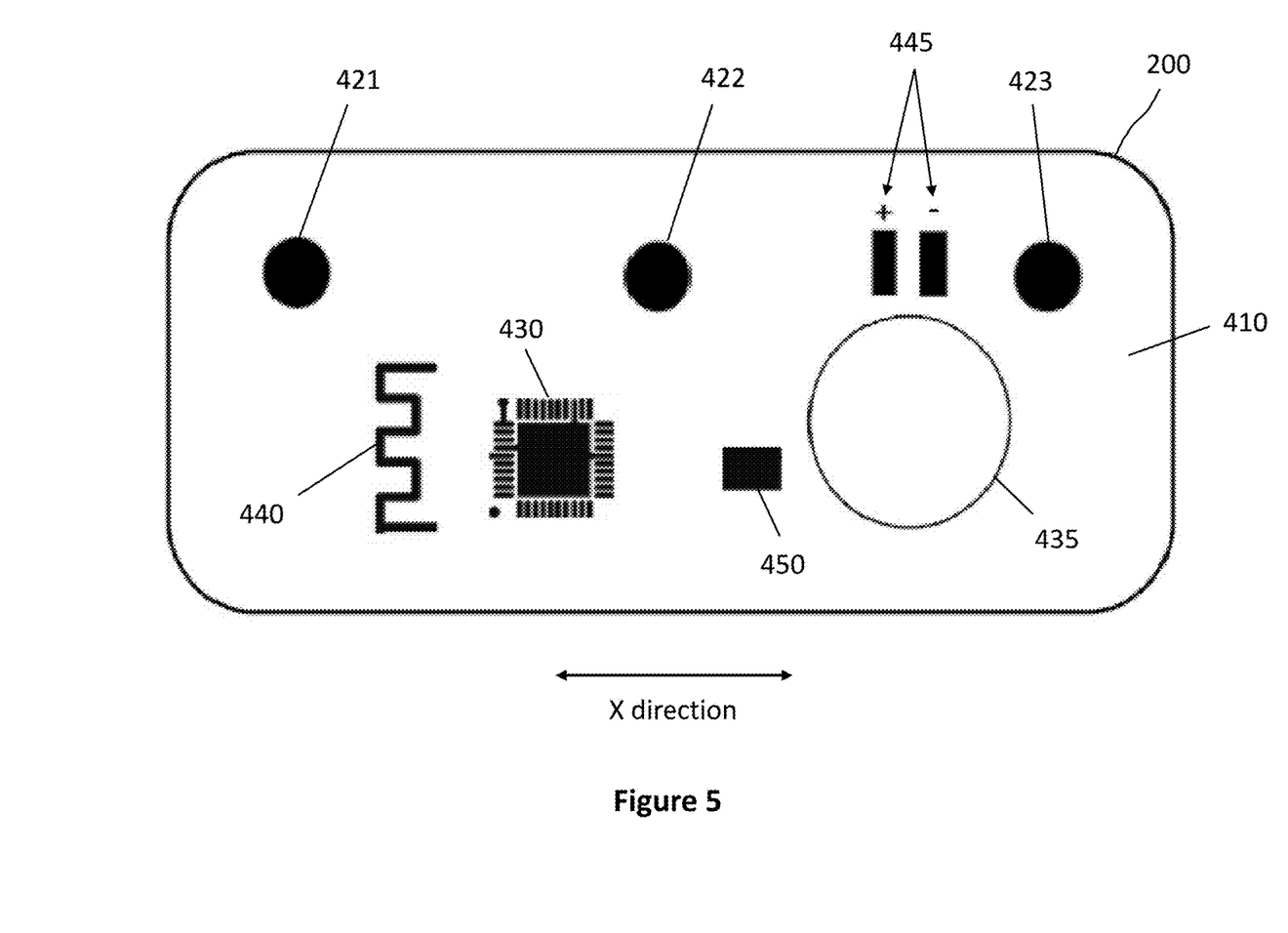
FIG. 5 is a top view of the wearable thermometer patch in FIG. 4.
Figure 6:
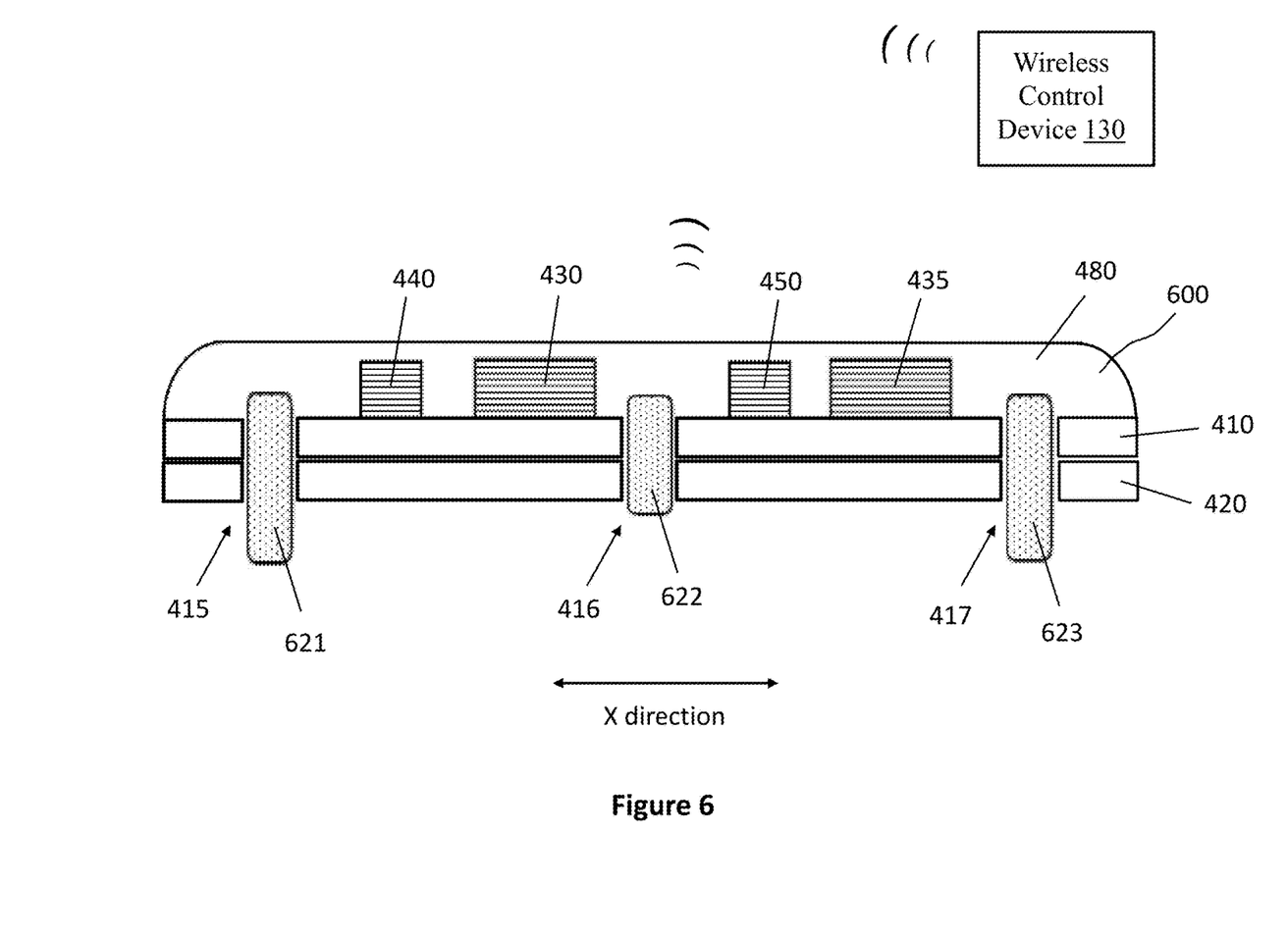
FIG. 6 is a cross-sectional view of another wearable thermometer patch in accordance with some embodiments of the present invention.

In some embodiments, referring to FIG. 6, a wearable thermometer patch 600 includes temperature sensor units 621, 622, 623 respectively positioned in the through holes 415-417, and various other components similar to those in the wearable thermometer patch 200 (FIGS. 4 and 5). The temperature sensor units 621, 622, 623 each includes at least one temperature sensor configured to measure a user's skin temperature at a different position along the x direction. The temperature sensor units 621, 622, 623 have different protrusion lengths out of the lower layer 420, which allows them to measure user's skin temperatures at different depths into the user skin.

It should be noted that the wearable thermometer patch 600 can include two, three, or more temperature sensors having different protrusion lengths out of the lower layer 420. In some embodiments, the temperature sensor units 621, 622, 623 can be disposed in a linear array in the plane parallel to the flexible circuit substrate 410 and the lower layer 420.

The different depths into a user's skin as well as the different positions along the x direction allow not only the calculation of a temperature gradient along the x direction, but also a determination of a temperature distribution into the depth of a user's skin. The temperature distribution into the depth of the user's skin provides additional information about the wound on user's skin, which makes the monitoring of wound healing more accurate.

It should also be noted that the wearable thermometer patch 600 is applicable to user skin measurement beyond monitoring wound healing. For example, the wearable thermometer patch 600 can be used to monitor a user's health such as a fever or a woman user's body temperature variations during menstrual cycles.

Figure 7:
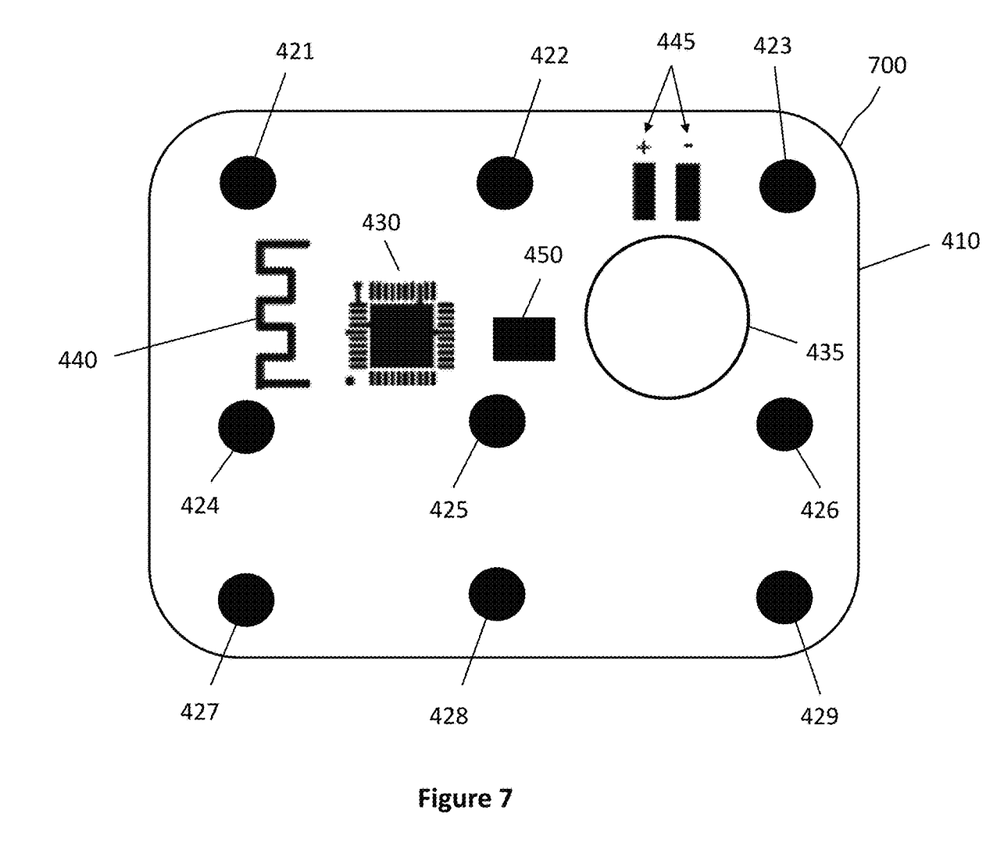
FIG. 7 is a top view of another wearable thermometer patch in accordance with some embodiments of the present invention.

In some embodiments, referring to FIG. 7, a wearable thermometer patch 700 includes temperature sensor units 421-429 in addition to various other components similar to those in the wearable thermometer patch 200 (FIGS. 4 and 5). Each of the temperature sensor units 421-429 includes at least one temperature sensor configured to measure a user's skin temperature at a different position. The temperature sensor units 421-429 are disposed in an area, rather than along a single straight line, across the plane parallel to the flexible circuit substrate 410 and the lower layer 420.

In some implementation, the temperature sensor units 421-429 are distributed in a two-dimensional array in the plane parallel to the flexible circuit substrate 410 and the lower layer 420. In some embodiments, the wearable thermometer patch includes four or more temperature probe units positioned in a two-dimensional array.

It should also be noted that the wearable thermometer patch 700 is applicable to user skin measurement beyond monitoring wound healing. For example, the wearable thermometer patch 700 can be used to monitor a user's health such as a fever or a woman user's body temperature variations during menstrual cycles. The temperature sensor units distributed in a two-dimensional area can reduce measurement errors and suppress effect of noise, which allows more accurate skin temperature measurements.

One advantageous feature of having the temperature sensor units spreading across an area in the planar directions of the wearable thermometer patch 700 is that it allows calculation of a temperature distribution across the two dimensions in the plane parallel to the flexible circuit substrate 410 and the lower layer 420. The two-dimensional temperature distribution across the user's skin provides additional information about the wound on user's skin, which makes the monitoring of wound healing more accurate. Temperature gradients away or toward the wound on the user's skin can be calculated based on the temperature values measured by the temperature sensor units 421-429 or based on the two-dimensional temperature distribution across the user's skin.

Another advantageous feature of having the temperature sensor units spreading across an area in the planar directions is that the wearable thermometer patch 700 is not sensitive to the orientation in which it is placed relative to a wound on user's skin. In contrast to some of the wearable thermometer patches disclosed above, one or more wearable thermometer patch 700 can be placed near a wound or at a reference position (as described above in relation to the wearable thermometer patch 200) at any orientations relative to the wound, which makes it more convenient to attach the wearable thermometer patch 700 to a user's skin for monitoring wound healing.

Referring to FIGS. 3, 6, 7, the local skin temperatures at different locations measured by the temperature sensor units in the wearable thermometer patch 600, 700 can be stored in the memory 450 and are used to calculate a temperature gradient as a function of the distance from the wound 125. The calculations can be conducted by firmware on the wearable thermometer patch 600 or 700, or software on the wireless control device 130. During the healing process, the temperature at a skin location closer to the wound is higher than that at a skin location further away from the wound, that is, the temperature gradient is positive toward the wound. The temperature gradient will gradually decrease to below a threshold (reflecting natural skin temperature variations) as the wound heals to a complete recovery.

The treatment plan storage 165 can store a normal range for the temperature gradient as a function of healing time for the skin temperatures near a wound. If the intelligent analyzer 190 determines that the calculated temperature gradient based on the measured temperature data is not within a normal range at a specific healing time, the wireless control device 130 can send out an alert to the user or a medical professional. The treatment control data can be stored in the memory 450.

In some embodiments, a second wearable thermometer patch can be attached to a similar skin location on the opposite side of the user body. Similar to the description above, the second wearable thermometer is so positioned that its associated x-direction is substantially perpendicular to the wound. Temperatures measured by the different temperature sensing units in this wearable thermometer patch can be used to calculate a baseline temperature gradient, which can be used to set the alert threshold.

In FIGS. 1-7, the wearable thermometer patch 200, or 600, or 700 can operate individually, or a group of wearable thermometer patches 200 can provide certain desired treatment or measurement. For example, multiple wearable thermometer patches 200, or 600, or 700 can be attached at locations on the opposite sides or several different sides of the wound 215, which can provide more accurate and comprehensive temperature monitoring around the wound 215. Furthermore, one of multiple wearable thermometer patches 200, or 600, or 700 can be placed in a symmetric skin position with no wound to provide live reference temperature data and comparison temperature gradient. For example, if the left leg has a wound, in addition to one or more wearable thermometer patches 200, or 600, or 700 dedicated to measure temperature around the wound 215, one or more wearable thermometer patches 200, or 600, or 700 can be attached to the symmetric positions on the right leg to provide temperature measurements and comparative temperature gradients.

The wearable thermometer patch 200, or 600, or 700 can also include a treatment portion to assist the wound healing process. The treatment portion can include heaters that can produce heat in target areas near the wound, or electromechanical actuators can produce electric or mechanical signals around the wound. The treatment signals are often applied in pulses. The treatment of wound is under the control of a treatment plan stored in the treatment plan storage 165 in the wireless control device 130. Using the measurement data and optionally historic user data, the intelligent analyzer 180 identifies improvement, issues, and risks in the user based on the measurement data to generate an analysis result, which could lead to timely reporting to the user or a central server, timely treatment, and/or improvement in the existing treatment. A portion of the analysis functions can be accomplished by a network server in communication with the wireless control device 130. Based on the analysis result, the treatment controller 160 can vary a type (e.g. heat or electric voltage), timing, a frequency, or duration of the treatment field in the user's body by the wearable thermometer patches.

The mode controller 170 plays a particular important role in dynamic treatments and dynamic measurements. The mode controller 170 can mobilize the treatment units to switch on a treatment mode in response to measurement data collected by the sensing units. Conversely, the mode controller 170 can mobilize sensing units and switch on measurement modes in the wearable thermometer patches in response to treatments applied to the user by the treatment units in the wearable thermometer patches.

Details of wearable patches for conducting measurements and treatments by one or a group of wearable sensors are disclosed in the commonly assigned co-pending U.S. patent application Ser. No. 15/649,008 titled "A system of networked wearable patches for measurement and treatment", filed Jul. 13, 2017, the disclosure of which is incorporated herein by reference.

The disclosed wearable thermometer patches have one or more of the following advantages. The disclosed wearable thermometer patch is stretchable, compliant, durable, conforming, and comfortable to wear by user's skin. The disclosed wearable thermometer patch is noninvasive and can be generically applied to monitor healing of different types of wounds. The disclosed wearable thermometer patch is capable of maximum continuous monitoring of user's temperature during the wound healing process. The measurement data can also be wirelessly communicated with external devices, which allows wound healing to be monitored in real time. The disclosed wearable thermometer patch can also provide some treatments to help the recovery of the wound and functions nearby. The disclosed wearable thermometer can also have a disposable and a reusable part to make wound healing extremely cost-effective.

In some embodiments, the wearable thermometer patch 200, 600, or 700 disclosed can be implemented as part of a wound dressing. The disclosed wearable thermometer patches and control devices can continuously monitor skin temperature at one or multiple locations, in a two dimensional area, and/or at different depths into user's skin.

The disclosed wearable thermometer patches can also include electronic components such as the semiconductor chips, resistors, capacitors, inductors, diodes (including for example photo sensitive and light emitting types), other types of sensors, transistors, amplifiers. The sensors can also measure temperature, acceleration and movements, and chemical or biological substances. The electronic components can also include electromechanical actuators, chemical injectors, etc. The semiconductor chips can perform communications, logic, signal or data processing, control, calibration, status report, diagnostics, and other functions.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination.

Moreover, although features may be described above as acting in certain combinations and even initially claimed as such, one or more features from a claimed combination can be excised from the combination in some cases, and the claimed combination may be directed to a sub-combination or a variation of a sub-combination.

Only a few examples and implementations are described. Other implementations, variations, modifications and enhancements to the described examples and implementations may be made without deviating from the spirit of the present invention.

What is claimed is:

1. A wearable thermometer patch for monitoring temperature on a user's skin, comprising:
    a circuit substrate comprising an electric circuit;
    a first temperature probe unit comprising a first temperature sensor in electric connection with the electric circuit in the circuit substrate, wherein the first temperature probe unit includes a first protruded portion below the circuit substrate;
    a second temperature probe unit comprising a second temperature sensor in electric connection with the electric circuit in the circuit substrate, wherein the second temperature probe unit includes a second protruded portion below the circuit substrate,
    wherein the first protruded portion and the second protruded portion have different protrusion lengths below the circuit substrate; and
    a treatment portion mounted on the circuit substrate and configured to apply heat, an electrical signal, or a force or a pressure to a user's skin,
    wherein the first temperature probe unit and the second temperature probe unit are configured to measure temperature values at different depths against the user's skin in response to the heat, the electrical signal, or the force applied to the user's skin by the treatment portion.

2. The wearable thermometer patch of claim 1, further comprising:
    a third temperature probe unit comprising a third temperature sensor in electric connection with the electric circuit, wherein the third temperature probe unit includes a third protruded portion below the circuit substrate.

3. The wearable thermometer patch of claim 1, further comprising:
    a lower layer below the circuit substrate, wherein the circuit substrate and the lower layer include through holes in which the first temperature probe unit and the second temperature probe unit are respectively mounted, wherein the first protruded portion and the second protruded portion are respectively configured to be in contact with the user's skin at different positions.

4. The wearable thermometer patch of claim 3, further comprising:
    an elastic layer on the circuit substrate, the first temperature probe unit, and the second temperature probe unit; and
    an adhesive material under the lower layer and configured to bond the lower layer to the user's skin.

5. The wearable thermometer patch of claim 1, wherein the first temperature probe unit includes a thermally conductive cup having a bottom portion configured to be in contact with the user's skin, wherein the first temperature sensor is placed inside and in thermal conduction with the thermally conductive cup.

6. The wearable thermometer patch of claim 1, further comprising:
    a semiconductor chip mounted on the circuit substrate and in electric connection with the electric circuit, wherein the semiconductor chip is configured to receive a first electrical signal from the first temperature sensor in response to a first measured skin temperature at the first position, wherein the semiconductor chip is configured to receive a second electrical signal from the second temperature sensor in response to a second measured skin temperature at the second position.

7. The wearable thermometer patch of claim 6, further comprising:
    an antenna mounted on the circuit substrate and in electric connection with the semiconductor chip, wherein the antenna is configured to wirelessly send temperature measurement data to a control device.

8. The wearable thermometer patch of claim 1, wherein the first temperature probe unit is located at a first position along a first direction, wherein the second temperature probe unit is located at a second position along the first direction, wherein the wearable thermometer patch is to be attached near a wound on a user's skin with the first direction is toward or away from the wound, wherein a temperature gradient is calculated based on the temperature values at the different distances.

9. The wearable thermometer patch of claim 8, wherein the first direction is substantially perpendicular to the wound on the user's skin.

10. The wearable thermometer patch of claim 8, wherein the treatment portion is configured to apply heat, an electrical signal, or a force or a pressure to user's skin to assist healing of the wound.

11. A wearable thermometer patch for monitoring temperature on a user's skin, comprising:
    a circuit substrate comprising an electric circuit;
    a treatment portion mounted on the circuit substrate and configured to apply heat, an electrical signal, or a force or a pressure to user's skin; and
    a plurality of temperature probe units mounted on the circuit substrate and distributed in a two-dimensional array in a plane parallel to the circuit substrate,
    wherein each of the plurality of temperature probe units comprises a temperature sensor in electric connection with the electric circuit in the circuit substrate,
    wherein the plurality of temperature probe units are configured to measure temperature values on a user's skin at different positions defined by the two-dimensional array.

12. The wearable thermometer patch of claim 11, wherein the plurality of temperature probe units include at least four temperature probe units.

13. The wearable thermometer patch of claim 12, further comprising:
    a lower layer below the circuit substrate, wherein the circuit substrate and the lower layer include through holes in which the plurality of temperature probe units are respectively mounted, wherein the plurality of temperature probe units include portions respectively configured to be in contact with the user's skin.

14. The wearable thermometer patch of claim 13, further comprising:
    an elastic layer on the circuit substrate, and the plurality of temperature probe units; and
    an adhesive material under the lower layer and configured to bond the lower layer to the user's skin.

15. The wearable thermometer patch of claim 1, wherein one of the plurality of temperature probe units includes a thermally conductive cup having a bottom portion configured to be in contact with the user's skin, wherein the one of one of the plurality of temperature probe units is placed inside and in thermal conduction with the thermally conductive cup.

16. The wearable thermometer patch of claim 1, further comprising:
   a semiconductor chip mounted on the circuit substrate and in electric connection with the electric circuit, wherein the semiconductor chip is configured to receive electrical signals from the plurality of temperature probe units in response to skin temperatures measured at different positions on the user's skin.

17. The wearable thermometer patch of claim 16, further comprising:
   an antenna mounted on the circuit substrate and in electric connection with the semiconductor chip, wherein the antenna is configured to wirelessly send temperature measurement data to a control device.

18. The wearable thermometer patch of claim 11, wherein the wearable thermometer patch is to be attached near a wound on a user's skin, wherein a temperature gradient is calculated based on the temperature values measured by the plurality of temperature probe units.

19. The wearable thermometer patch of claim 18, wherein the temperature gradient is calculated by a semiconductor chip in the circuit substrate or by a control device in communication with the electric circuit.

20. The wearable thermometer patch of claim 18,
   wherein the temperature values are measured by the plurality of temperature probe units in response to the heat, the electrical signal, or the force applied to the user's skin by the treatment portion.

* * * * *